(12) United States Patent
Schertiger

(10) Patent No.: US 11,547,594 B2
(45) Date of Patent: Jan. 10, 2023

(54) OSTOMY DEVICE

(71) Applicant: Coloplast A/S, Humlebaek (DK)

(72) Inventor: Lars Olav Schertiger, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 820 days.

(21) Appl. No.: 16/335,254

(22) PCT Filed: Sep. 21, 2017

(86) PCT No.: PCT/DK2017/050304
§ 371 (c)(1),
(2) Date: Mar. 21, 2019

(87) PCT Pub. No.: WO2018/054442
PCT Pub. Date: Mar. 29, 2018

(65) Prior Publication Data
US 2020/0015996 A1     Jan. 16, 2020

(30) Foreign Application Priority Data
Sep. 21, 2017   (DK) .......................... PA 2016 70741

(51) Int. Cl.
*A61F 5/44*  (2006.01)
*A61F 5/443*  (2006.01)

(52) U.S. Cl.
CPC ............ *A61F 5/4401* (2013.01); *A61F 5/443* (2013.01)

(58) Field of Classification Search
CPC ........ A61F 5/4401; A61F 5/443; A61F 5/445; A61F 5/44
See application file for complete search history.

(56) References Cited

U.S. PATENT DOCUMENTS

| | | | |
|---|---|---|---|
| 3,902,496 A | | 9/1975 | Eakin |
| 5,722,965 A | * | 3/1998 | Kuczynski .............. A61F 5/443 |
| | | | 604/338 |
| 5,733,271 A | * | 3/1998 | Bjo ......................... A61F 5/441 |
| | | | 55/482 |
| 5,912,059 A | * | 6/1999 | Jones ....................... A61F 5/443 |
| | | | 428/35.5 |
| 6,071,268 A | * | 6/2000 | Wagner ................... A61F 5/445 |
| | | | 604/338 |

(Continued)

FOREIGN PATENT DOCUMENTS

| | | |
|---|---|---|
| CN | 101401733 A | 4/2009 |
| CN | 201727625 U | 2/2011 |

(Continued)

*Primary Examiner* — Guy K Townsend
(74) *Attorney, Agent, or Firm* — Coloplast Corp., Coloplast A/S; Nick Baumann

(57) ABSTRACT

An adhesive ostomy element comprising a backing layer (3) and having at least a first section (1) and at least a first adhesive (4) on a surface of said backing layer. In the centre is provided a stoma-receiving through-going hole (2) defining an inner boundary in said first section and said first section being adjacent to and extending radially from said through-going hole. At least a part of the portion of the first section is provided with a layer of absorbent foam (7) adjacent the hole. The foam expands towards the stoma when wetted and provides a seal against the stoma.

16 Claims, 4 Drawing Sheets

(56) References Cited

U.S. PATENT DOCUMENTS

| | | | | |
|---|---|---|---|---|
| 6,602,232 B1* | 8/2003 | Keyes | ................... | A61F 5/448 604/338 |
| 8,319,003 B2* | 11/2012 | Olsen | ................. | A61F 13/0269 604/338 |
| 8,439,884 B2* | 5/2013 | Fabo | ..................... | A61F 5/445 604/338 |
| 8,545,468 B2* | 10/2013 | Fabo | ..................... | A61L 24/046 604/338 |
| 8,697,932 B2* | 4/2014 | Tunius | ................. | A61L 15/585 602/41 |
| 8,957,277 B2* | 2/2015 | Carty | ..................... | A61L 15/42 602/41 |
| 11,109,996 B2* | 9/2021 | Stroebech | ............... | A61F 5/445 |
| 2004/0006320 A1* | 1/2004 | Buglino | ................. | A61F 5/448 604/344 |
| 2007/0282284 A1* | 12/2007 | Mullejans | ............... | A61F 5/441 604/333 |
| 2008/0097361 A1* | 4/2008 | Fabo | ..................... | A61F 5/445 604/338 |
| 2009/0093682 A1 | 4/2009 | Izzo et al. | | |
| 2009/0312685 A1* | 12/2009 | Olsen | ................. | A61F 13/0269 604/386 |
| 2010/0114044 A1* | 5/2010 | Cramer | ................. | A61F 5/448 604/332 |
| 2010/0191204 A1* | 7/2010 | Bach | ................... | A61L 24/0031 604/344 |
| 2010/0198176 A1* | 8/2010 | Stroebech | ............... | A61L 24/04 523/105 |
| 2010/0204665 A1* | 8/2010 | Stroebech | ............... | A61F 5/445 604/344 |
| 2010/0324511 A1* | 12/2010 | Dove | ..................... | A61F 5/445 604/338 |
| 2011/0034890 A1* | 2/2011 | Stroebech | ............... | A61L 24/043 604/336 |
| 2011/0092929 A1 | 4/2011 | Weig | | |
| 2011/0177329 A1* | 7/2011 | Xia | ..................... | C09J 133/00 428/354 |
| 2011/0218507 A1* | 9/2011 | Andersen | ................ | A61F 5/445 604/338 |
| 2011/0224593 A1* | 9/2011 | Tunius | ................. | A61L 15/585 522/66 |
| 2012/0143155 A1* | 6/2012 | Edvardsen | ............. | A61F 5/443 604/318 |
| 2013/0004749 A1* | 1/2013 | Hao | ..................... | B32B 29/00 428/206 |
| 2013/0017246 A1* | 1/2013 | Tunius | ................ | A61F 13/0206 522/66 |
| 2013/0026117 A1 | 1/2013 | Hardy | | |
| 2013/0123678 A1* | 5/2013 | Carty | ................. | A61F 13/0253 602/54 |
| 2013/0133532 A1* | 5/2013 | Kian | ..................... | C09J 7/385 428/354 |
| 2013/0138065 A1* | 5/2013 | Buus | ..................... | A61F 5/443 604/344 |
| 2013/0226116 A1* | 8/2013 | Edvardsen | ............. | A61F 5/443 604/338 |
| 2013/0226117 A1* | 8/2013 | Hansen | ............... | A61L 24/0036 604/338 |
| 2013/0274696 A1* | 10/2013 | Lam | ..................... | A61L 24/046 604/332 |
| 2013/0304008 A1 | 11/2013 | Hanuka et al. | | |
| 2014/0114265 A1* | 4/2014 | Israelson | ................ | A61F 5/443 604/342 |
| 2014/0128826 A1* | 5/2014 | Klein | ..................... | A61F 5/443 604/344 |
| 2014/0316324 A1* | 10/2014 | Wibaux | ............... | A61F 13/0253 602/56 |
| 2015/0030839 A1* | 1/2015 | Satrijo | ..................... | C08L 53/00 428/220 |
| 2016/0199230 A1* | 7/2016 | Doshi | ..................... | A61F 13/58 156/219 |
| 2016/0256665 A1* | 9/2016 | Doshi | ..................... | A61F 5/445 |
| 2018/0008451 A1* | 1/2018 | Stroebech | ............... | A61F 5/448 |
| 2018/0021474 A1* | 1/2018 | Stroebech | ............... | A61F 5/448 604/336 |
| 2018/0116859 A1* | 5/2018 | Strøbech | ................. | A61F 5/445 |
| 2018/0263804 A1* | 9/2018 | Stroebech | ............... | A61F 5/443 |
| 2019/0070034 A1* | 3/2019 | Udayakumar | ........ | A61L 24/043 |
| 2020/0015996 A1* | 1/2020 | Schertiger | ............ | A61F 5/4401 |
| 2021/0369487 A1* | 12/2021 | Stroebech | ............... | A61F 5/445 |

FOREIGN PATENT DOCUMENTS

| | | | | |
|---|---|---|---|---|
| CN | 104644310 A | 5/2015 | | |
| CN | 105407841 A | 3/2016 | | |
| EP | 0710094 A1 * | 5/1996 | ............ | A61F 5/441 |
| EP | 0710094 A1 | 5/1996 | | |
| EP | 0984751 B1 | 7/2002 | | |
| GB | 2277031 A1 | 10/1994 | | |
| NL | 8902835 A | 6/1991 | | |
| RU | 2220685 C1 | 1/2004 | | |
| WO | 9503015 A1 | 2/1995 | | |
| WO | 9960959 A1 | 12/1999 | | |
| WO | WO-9960959 A1 * | 12/1999 | ............ | A61F 5/443 |
| WO | WO-199960959 A2 * | 12/1999 | ............ | A61F 5/443 |
| WO | 2014117778 A1 | 8/2014 | | |
| WO | WO-201411778 A2 * | 8/2014 | ............ | A61F 5/443 |
| WO | WO-2014117778 A1 * | 8/2014 | ............ | A61F 5/443 |
| WO | 2017059869 A1 | 4/2017 | | |

* cited by examiner

OSTOMY DEVICE

SUMMARY OF THE INVENTION

One aspect provides an adhesive ostomy element comprising a backing layer, having at least a first section. The element has at least a first adhesive on a surface of said backing layer and a stoma-receiving through-going hole defining an inner boundary in said first section. The first section is adjacent to and extends radially from said through-going hole. At least a part of a portion of the first section is provided with a layer of absorbent foam adjacent the hole to the inner boundary. When the foam is wetted, it expands towards the stoma to provide a sealing.

DETAILED DESCRIPTION OF THE INVENTION

Figure 1:
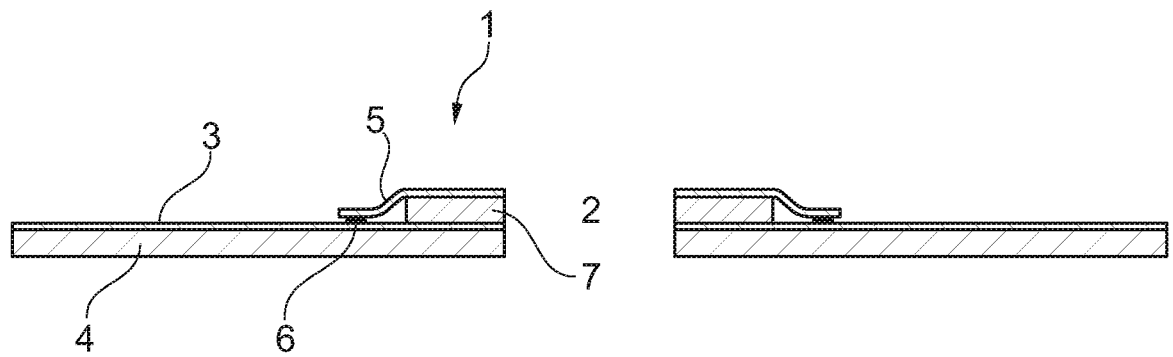
In FIG. 1 is shown a cross-section of an embodiment of an adhesive element in dry state, In FIG. 2 is shown the embodiment of FIG. 1 in wet state, In FIG. 3 is shown an embodiment before wetting and In FIG. 4 is shown the embodiment of FIG. 3 after wetting In FIGS. 5 and 6 are shown an embodiment with a moldable paste under the foam layer.

For interpretations in the context of the present application, some definitions regarding the subject matter of the attached claims are presented below.

When referring to the proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The radial direction, or radially, is defined as transverse to the axial direction that is transversely to the direction of the stoma.

"Release liner" is intended to define a liner covering the proximal (skin contacting) side of the adhesive that ensures at least that the properties of the adhesive are preserved and that the adhesive surface is not laid open until just before the use.

When addressing the dimensions of the foam layer herein it is understood to be dry foam unless otherwise stated.

In embodiments, the ostomy element may be a part of an ostomy base plate. It may be integrated in a base plate or it may be a separate element to be combined with a base plate.

An aspect provides an adhesive ostomy element comprising a backing layer, having at least a first section, and having at least a first adhesive on a surface of said backing layer, a stoma-receiving through-going hole defining an inner boundary in said first section, said first section being adjacent to and extending radially from said through-going hole, at least a part of the portion of the first section being provided with a layer of absorbent foam adjacent to the hole to the inner boundary, wherein the foam expands towards the stoma when wetted.

In embodiments is provided an ostomy base plate comprising a backing layer, having a first section and a second section, and having at least a first adhesive on a surface of said backing layer, a stoma-receiving through-going hole defining an inner boundary in said first section, said first section being adjacent to and extending radially from said through-going hole and said second section surrounding said first section defining an outer boundary of the base plate, at least a part of a portion of the first section being provided with a layer of swellable, absorbent foam adjacent to the hole to the inner boundary, wherein the foam is configured to expand towards the stoma when wetted.

In embodiments, the foam layer may be flush with the inner boundary of the through-going hole. By flush is herein meant that the foam, in dry state, and the underlying adhesive layer have the same inner boundary towards the stoma, i.e. the foam does not extend further inwards than the boundary of the through-going hole of the element. When the foam is wetted, for example by the effluent from the stoma, the foam will expand and will then extend further than the boundary of the element, thereby facilitating a seal around the stoma.

In embodiments, the foam layer may have an inner radius being larger than the radius of the through-going hole. When the foam is wetted and absorbs water, it may expand towards the hole to have a diameter being less than the through-going hole.

In embodiments, the foam may expand at least 50% v/v, such as 100% v/v, such as 200% v/v, such as at least 300% v/v or even at least 400% v/v when fully saturated with water. The expansion is measured by determining the dimensions of a foam sample, placing the sample in saline water for 24 hours and then measure dimensions again.

In embodiments, the foam may contain absorbent particles. In embodiments, the absorbent material is selected from hydrocolloid, water soluble salt, mono, di- and oligo-saccharides or super absorbent particles (polyacrylate).

In embodiments, the foam layer expands to reduce the size of the through-going hole by at least 5%, such as by at least 10% when the foam is fully saturated with water. The size of the hole is measured in radial direction; thus, the radius of the hole is reduced when the foam expands.

The foam swells when absorbing aqueous liquids. Such liquids may be aqueous liquids such as output from a stoma, or other physiological liquids or water or saline.

In embodiments, the foam layer is located adjacent to the distal surface of the backing layer.

In embodiments, the foam layer may be attached directly to the backing layer. The foam may be attached along its outer boundary or in discrete dots or lines. In embodiments, the foam may be unattached to the portion closest to the inner boundary in order to fully allow expansion inwardly when the foam is wetted.

In embodiments, the foam layer may be at least partly enclosed in an envelope. In embodiments, the envelope may comprise a cover layer. The cover layer of the envelope may comprise a distal and a proximal sheet being connected along the outer rim or the cover layer. In embodiments, the backing layer or part thereof may constitute either the distal or the upper or the lower sheet of the cover layer.

In embodiments, a sealing device comprises an envelope enclosing a foam layer, a through-going hole for receiving a stoma in the central portion of the envelope, the envelope is provided with adhesive on either the proximal or the distal surface of the envelope and wherein the foam is expanding towards the through-going hole when wetted. Such sealing device may be a separate unit that may be combined with an ostomy base plate. In embodiments, the envelope may be placed on the distal side of the backing layer or it may be placed on the proximal side of the base plate.

The envelope may be provided on the distal surface of the backing layer. The envelope may be in the form of a cover layer overlying the foam layer on at least one surface and being attached to the backing film by welding or adhesive along the outer boundary.

In embodiment, the envelope may be provided with adhesive on one surface for attachment to a base plate or to the skin. The adhesive may be a continuous layer or discontinuous such as in a pattern or discrete dots. The envelope may be open towards the boundary surrounding the through-going hole.

In embodiments, the distal sheet of the cover layer may have an inner rim of a larger radius than the inner boundary of the element. This may allow moisture to rapidly contact the foam and initiate the swelling and sealing. In embodiments, the cover layer may be provided with slits or perforations.

In embodiments, the envelope may have an outer boundary corresponding essentially to the outer boundary of the foam or it may have an outer boundary being larger than the foam. Enclosing the foam in an envelope being approximately the same size as the dry foam may force the expansion of wetted foam to pass through the opening of the envelope, being the opening along the inner boundary and against the stoma, thus the expansion will mainly be axially inwards.

In embodiments, the envelope is larger than the foam layer, facilitating that the envelope has room for the outwards expansion of the foam layer too.

In embodiments, the foam may be attached in the envelope or it may not be attached in the envelope, i.e. unattached and thereby free floating in the envelope. An unattached foam may allow the foam to perform a degree of self-centering to the stoma.

In embodiments, the cover layer is a fabric, non-woven, net, polymeric film. The cover layer may be made from any suitable material such as polypropylene, polyethylene, polyethylene terephthalate, ethylene vinyl acetate or other aliphatic polymer systems.

In embodiments, the cover layer may be permeable to liquid. The cover layer may be an impermeable film provided with slits, holes or perforations. The perforations may be in a uniform pattern of they may be designed in such a way that the part of the cover layer being closest to the stoma is provided with more/or larger holes than the peripheral portion of the cover layer in order to allow this part of the foam to swell first.

In embodiments, the cover layer is impermeable. Liquid may enter the foam through the inner boundary of the stoma-receiving hole. The element may be fitted around a stoma and an adhesive base plate is placed over the element. When the cover layer is impermeable, the absorbed liquid in the foam cannot penetrate into the adhesive of the base plate.

In embodiments, the cover layer partly covers the foam layer. In embodiments, the cover layer fully covers the foam layer.

In embodiments, the distal sheet of the cover layer may have an inner rim of a larger radius than the inner boundary of the element. This may allow moisture to rapidly contact the foam and initiate the swelling and sealing. In embodiments, the cover layer may be provided with slits or perforations.

The foam may be any water swellable foam. In embodiments, the foam comprises polyurethane foam. Other suitable foam may be polypropylene, polyethylene, polyether or other aliphatic polymers being capable of expanding when absorbing water.

In embodiments, the foam layer may have a thickness of 0.2-5 mm, such as 0.5-4 mm, such as 0.5-3 mm or even such as 0.5-2 mm.

The outer boundary of the foam may be less than the radius for an attachment point of a collecting bag. In embodiments, the outer boundary of the foam layer fits inside a coupling ring for attaching a collecting bag.

Compared to hydrocolloid pastes and adhesives, the foam readily absorbs liquid resulting in fast swelling and thus quickly provides a tight seal around the stoma. The softness of the foam allows it to fit to irregular shapes of stoma without strangulating the stoma. The foam may be resistant to the output from the stoma and may thus not erode or wash out over time as hydrocolloid adhesive may do, but it may maintain its shape and integrity. The foam will thus stay in place and offer protection of the underlying adhesive during the entire wear time.

The softness of the foam facilitates that it can fit to a number of different shapes of the stoma, facilitating that a standard size element may fit to many different stomas without adapting the hole size by cutting. However, due to the construction it may be possible to adapt the hole by cutting, if necessary, for example with a very irregular stoma or for enlargement of the hole.

In embodiments, the foam layer may be provided with means for controlling the direction of the expansion of the foam. Providing a surface of the foam with a layer having an expansion, when wetted, being less than the expansion of the foam may force the foam to curve when swelling. This may be advantageous when fitting around a retracted stoma, where the foam may curve in proximal direction to fit around the retracted stoma or in distal direction to a protruding stoma. In embodiments, the foam is provided with a film on one surface, the film being less swellable than the foam. In embodiments, one surface of the foam is provided with welding that may reduce the expansion of this surface of the foam.

In embodiments, an absorbent layer over the foam may act as a wicking layer, quickly distributing the liquid over the entire foam layer and thereby speeding up the expansion process. Such absorbent layer may be a part of the cover layer or a separate layer.

Stomas exist in various shapes and sizes; some are more challenging to fit an adhesive element to than others. Some stomas have a shape like a mushroom, with a thin stem and a broader hat on top of it. Such stomas may be difficult to fit a base plate to, as a large hole may be needed in the base plate in order to pass the hat through, but such hole will be too large for the stem as this has a smaller diameter than the hat. Furthermore, there is a risk of contaminating the skin facing adhesive part of the base plate with effluent from the stoma when dragging a narrow hole over the stoma hat. The foam layer of the element may allow use of a larger hole in the plate, facilitating room for the hat to pass and when the foam expands during wetting it will fill the empty space between the inner boundary of the hole and the stem of the stoma.

The swellable foam being located around the stoma may cover the naked skin around the stoma resulting in improved skin condition and reduction of leakage as well as erosion of the adhesive is minimized.

The at least one release liner used in connection with the ostomy element may suitably be a siliconized or fluorinated liner, such as a siliconized or fluorinated craft paper, polyethylene, polypropylene or polyethylene terephthalate film.

In embodiments, a second section surrounds the first section of the ostomy element to constitute an ostomy base plate.

The base plate may be provided with a collection bag. The collection bag may be attached permanently to the base plate or it may be detachable from the base plate.

The ostomy base plate may comprise coupling means for attachment of a collection bag. The coupling means may be in the form of a mechanical coupling or it may be an adhesive coupling.

In embodiments, the adhesive element will have a proximal ("skin-facing") surface, which faces the skin of the user during use, and a distal ("non-skin-facing") surface, which faces away from the user's skin during use. Before use, the proximal surface of the adhesive element can be covered by a release liner, which is releasably attached to the adhesive. The release liner can be removed by the user immediately prior to application of the adhesive element to the skin. Both before and during use, the distal surface of the adhesive element can be made up of a backing layer, which can be used to attach the collecting bag to the adhesive element or base plate, for instance by welding.

The adhesive may be any suitable adhesive, such as rubber, polyurethane or acrylic, silicone adhesive. The adhesive may comprise absorbent particles.

The adhesive element may include an absorbent adhesive composition. The absorbent adhesive composition is capable of absorbing moisture. The purpose of having an absorbent adhesive composition as a part of an ostomy device is to allow the absorbent adhesive composition to absorb moisture produced by the skin and thereby prevent accumulation of moisture at the skin surface, underneath the ostomy device. Accumulation of moisture on the skin surface can lead to damage of the skin, such as maceration.

In embodiments, the adhesive composition comprises a polymer comprising monomer units selected from the group consisting of styrene, isoprene, butadiene, ethylene, and butylene.

In embodiments, the adhesive composition comprises a styrene block co-polymer.

In embodiments, the adhesive composition comprises a styrene block co-polymer selected from the group consisting of styrene-isoprene-styrene (SIS), styrene-butadiene-styrene (SBS), styrene-isobutylene-styrene (SIBS), and styrene-ethylene/butylene-styrene (SEBS).

In embodiments, the adhesive composition comprises a polyethylene copolymer.

In embodiments, the adhesive composition comprises a polyethylene copolymer selected from the group consisting of ethylene vinyl acetate, ethylene vinyl acetate carbon monoxide, ethylene butyl acetate, ethylene vinyl alcohol, ethylene butyl acrylate, ethylene butyl acrylate carbon monoxide, and combinations thereof.

In embodiments, the adhesive composition comprises polyisobutylene (PIB).

In embodiments, the adhesive composition comprises absorbent material selected from the group consisting of hydrocolloids, microcolloids, salt, and super absorbent particles.

In embodiments, the adhesive composition comprises an absorbent material in an amount of 1-60% (w/w) of the composition.

For instance, the adhesive composition comprises an absorbent material in an amount of 1-40% (w/w) or 1-20% (w/w) or 20-40% (w/w) or 20-60% (w/w) or 40-60% (w/w) or 25-50% (w/w) of the composition.

In embodiments, the absorbent material is selected from hydrocolloid, water soluble salt, mono, di- and oligosaccharides. In embodiments, the hydrocolloid is selected from guar gum, locust bean gum, pectin, potato starch, alginates, gelatine, xantan or gum karaya, cellulose derivatives, salts of carboxymethyl cellulose, sodium carboxymethyl cellulose, methyl cellulose, hydroxypropyl cellulose, hydroxyethyl cellulose, sodium starch glycolate, polyvinylalcohol, and mixtures thereof.

In embodiments, at least a part of the first section comprises a layer of moldable adhesive paste. The paste may be arranged around the through going hole of the base plate in a way that allows the paste to be dispensed towards the hole and stoma when pressure is applied to the layer of paste, e.g. by a finger. In embodiments, the paste is located between the foam layer and the backing layer. In embodiments, the paste layer may be placed on the skin-contacting surface of the element. In embodiments, the foam is superimposed over the paste layer.

In embodiments, a separating layer may be present between the foam layer and the paste layer in order to avoid the paste from unintentional migration into the foam layer. In embodiments, the paste layer is molded to fit around the stoma after application of the base plate, by pressing a finger towards the distal surface of the base plate in the area over the moldable layer.

In an aspect is provided an ostomy device comprising a collection bag and a base plate comprising an adhesive ostomy element comprising a backing layer, having at least a first section, and having at least a first adhesive on a proximal surface of said backing layer, a stoma-receiving through-going hole defining an inner boundary in said first section, said first section being adjacent to and extending radially from said through-going hole, at least a part of the distal portion of the first section being provided with a layer of absorbent foam adjacent to the hole to the inner boundary, wherein the foam expands towards the stoma when wetted.

In embodiments, the foam layer may be provided with radial slits, extending from the hole. In embodiments, the foam layer along the outer periphery may be continuous (not interrupted by slits).

In embodiments, the foam layer is an integrated part of an ostomy device. In embodiments, the foam layer is a separate unit that can be combined with an ostomy base plate by placing it on the distal side of the backing layer or it may be placed on the proximal side of the base plate.

In embodiments, a foam layer with slits are produced as an elongated strip with one straight, uninterrupted side edge and slits or cut-outs along another side edge. Before use, the strip can be cut in desired length and mounted at the baseplate, inside the connection zone to produce a circular foam sheet with flaps separated by slits. In embodiments, the base plate may be delivered with the foam element or the user may mount the foam element on the base plate. The flaps, separated by slits, facilitate snug fit to the stoma as well as it may allow the flaps to bend at the stoma to provide a collar around the stoma. The presence of flaps facilitates that the stoma will not be strangulated by the foam.

DETAILED DESCRIPTION OF THE DRAWINGS

In the following detailed description, reference is made to the accompanying drawings. The drawings form a part of this specification and illustrate exemplary embodiments for practicing the invention. Directional terminology, such as "top," "bottom," "front," "back," "leading," "trailing," etc., is used with reference to the orientation of the Figure(s) being described. Because components of embodiments can be positioned in a number of orientations, the directional terminology is used for purposes of illustration and is in no way limiting. It is to be understood that other embodiments may be utilized and structural or logical changes may be made without departing from the scope of the invention. The detailed description describes examples for practicing the invention and is not to be read to limit the scope of the invention. The scope of the invention is defined by the attached claims.

Embodiments, and features of the various exemplary embodiments described in this application, may be combined with each other ("mixed and matched"), unless specifically noted otherwise.

In FIG. 1 is shown a cross-sectional view of an embodiment of the ostomy element, the element comprising a first central portion 1 surrounding a hole 2 for accommodating a stoma. The element comprises a backing layer 3 coated on the skin-facing surface with an adhesive layer 4. On the non-skin-facing surface of the backing layer is provided a cover layer 5 surrounding the central hole 2. The cover layer is attached by welding or by adhesive along its outer boundary 6 to create a pocket or envelope being open towards the hole. In the envelope is a layer of foam 7. The inner boundary of the foam 7 is coinciding with the inner boundary of the adhesive 4 and backing layer 3.

Figure 2:
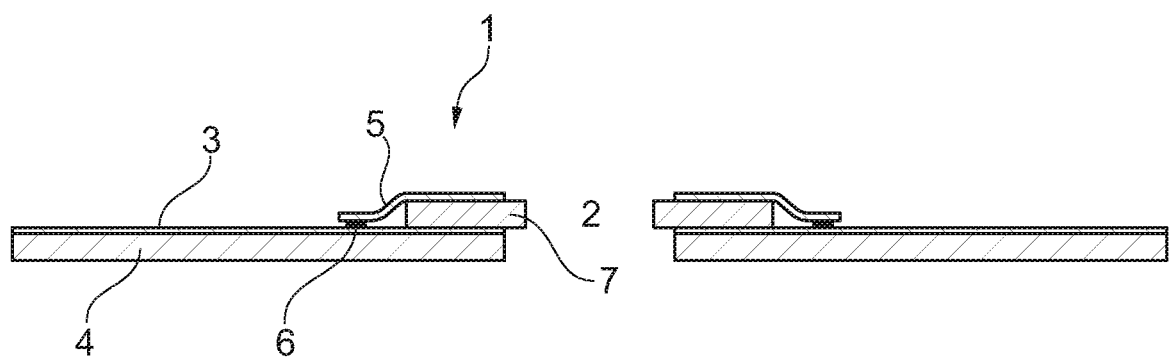

In FIG. 2 is shown the same embodiments as in FIG. 1 after the foam 7 has been exposed to liquid such as effluent from a stoma. The foam 7 has expanded into the hole of the element and may provide a snug fit to a stoma.

Figure 5:
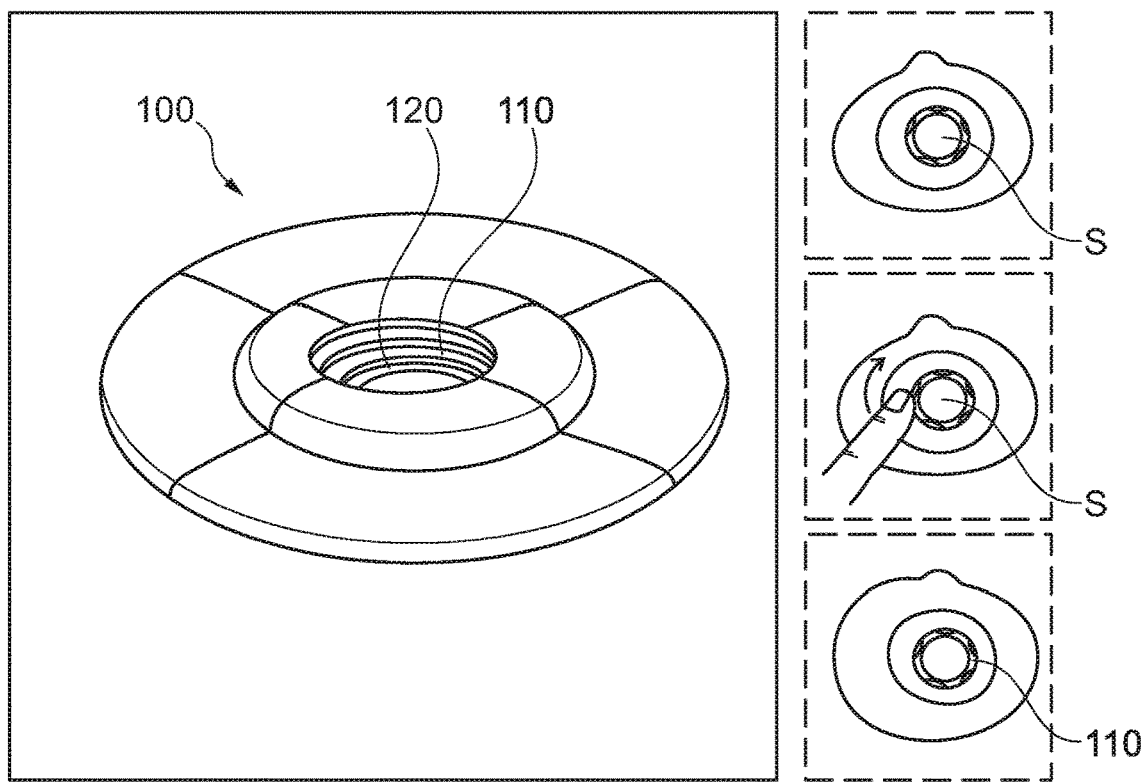

In FIG. 5 is shown an ostomy element 100 comprising a stoma S receiving hole and a layer of foam 110 surrounding the hole. The foam layer is overlying a layer of moldable paste 120 and the two layers 110, 120 are separated by a separating layer 130. On the distal side of the foam 110 may optionally be a pocket 140 of substantially same shape and area as the foam layer 120, the pocket 140 containing a fluid for wetting the foam 150. The pocket is ruptured when a finger F is slided over the pocket and at the same time applying a light pressure to the paste layer 120, thereby molding it to fit towards the stoma S and releasing the wetting fluid for expanding the foam.

The past layer may be in the form of separate concentric rings encircling the stoma receiving hole. The rings may be closed but rupturable by pressure from a finger.

Figure 6:
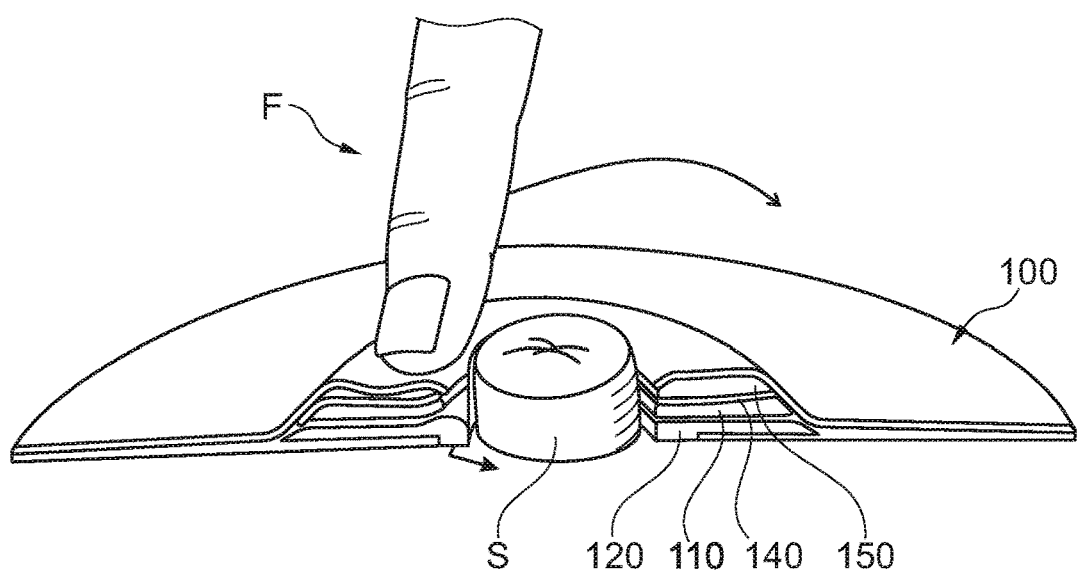

In FIG. 6 is shown an embodiment of an ostomy element 100. The element comprises a foam layer 160 provided with the slits extending from the hole 2 and partly to an outer periphery of the foam. The outer periphery of the foam may fit inside a coupling ring 170 for attachment of a collecting bag. Flaps are defined as the portion of foam layer between the slits.

Figure 7:
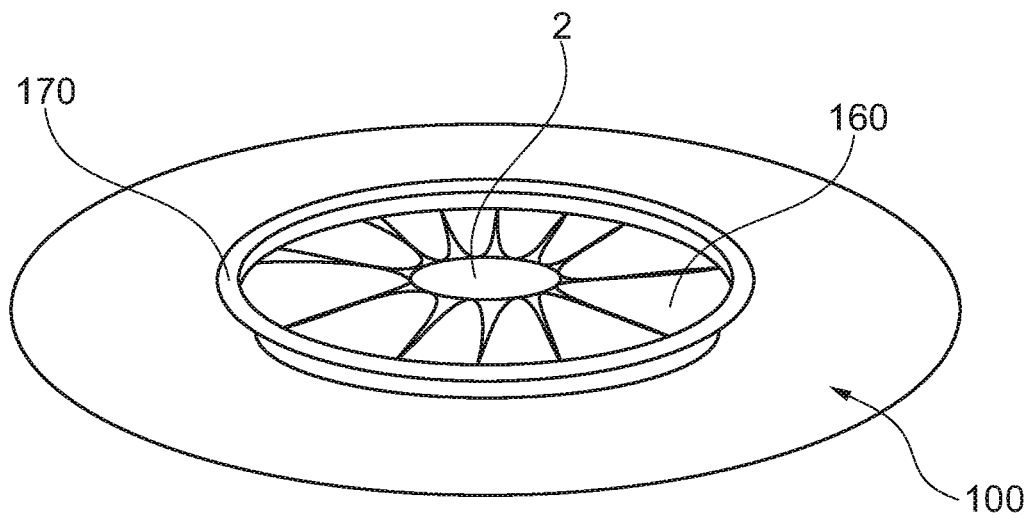
In FIG. 7 is shown and embodiment of an ostomy element on a base plate.
Figure 8:
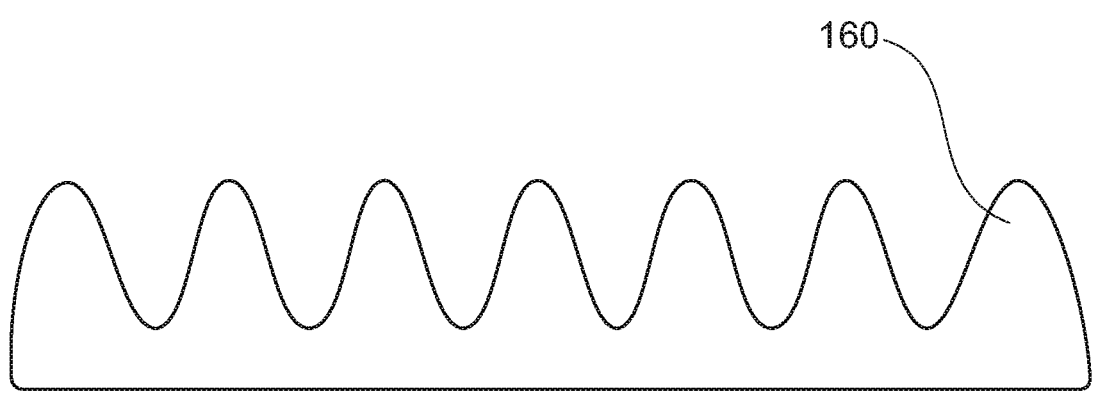
In FIG. 8 is shown and embodiment of an ostomy element.

In FIG. 7 is shown a foam layer 160 provided with slits in the form of cut-outs along one longitudinal edge. In embodiments, the strip can be cut into suitable length and curled to a circular shape with the edge with slits are facing towards the hole 2. The curled foam element may be mounted inside a coupling ring on an ostomy base plate.

EXAMPLES

The following samples were used for all tree examples:
Sample A: An "Assura" base plate from Coloplast.
Sample B: An ostomy base plate of the type "Assura" from Coloplast (Sample A) to which a layer of a 50 μm polyethylene foil was welded along its outer radius/periphery to the central portion of the base plate to provide an envelope being open towards the central hole of the plate. In the envelope was a 3.5 mm thick layer of polyurethane foam ("Biatain" from Coloplast). The inner boundary of the foam corresponded to the inner boundary of the plate.

Example 1

The sealing effect of an ostomy element was tested.
The test was carried out as follows. The test was conducted over 24 hours. A sample was placed in an incubator and fitted over an artificial stoma. Saline (0.9% NaCl in water) was filled to cover the sample completely. A magnetic stirrer provided motion of the saline. Temperature in the incubator was set to 37° C. The samples were left in the incubator for 24 hours.

After 24 hours, the saline over Sample A was inspected. The saline appeared blurred from residues of the adhesive, being washed out from the plate, and the adhesive of the base plate was clearly eroded. In sample B, the saline over Sample B was clear and the adhesive around the stoma was intact. The foam of Sample B had swollen to provide a snug fit against the artificial stoma and thus protected the adhesive beneath.

Example 2

Long Term Effect of Sealing
The same test conditions were used as in Example 1, but conducted over 9 days instead. Sample A without foam suffered from a large outwards erosion whereas the Sample B with foam showed only inwards swelling of the adhesive but none or very little erosion.

Example 3

Sealing Against an Irregular Stoma
A test was conducted to see how fast and how effective the element was sealing around an irregular stoma.
The test was carried out as follows. A sample with a circular hole was fitted over an artificial stoma having an irregular shape and saline was added continuously drop by drop by a pipette to the central portion of the base plate. The sample was observed over time.

After 2 minutes, the gap between the edges of Sample A and the irregular stoma is still the same, and the added saline lies as a pool of liquid in the space between the stoma and the base plate, thereby being a risk of maceration of the peristomal skin as well as the adhesive may be eroded or washed out.

Figure 3:
Figure 4:
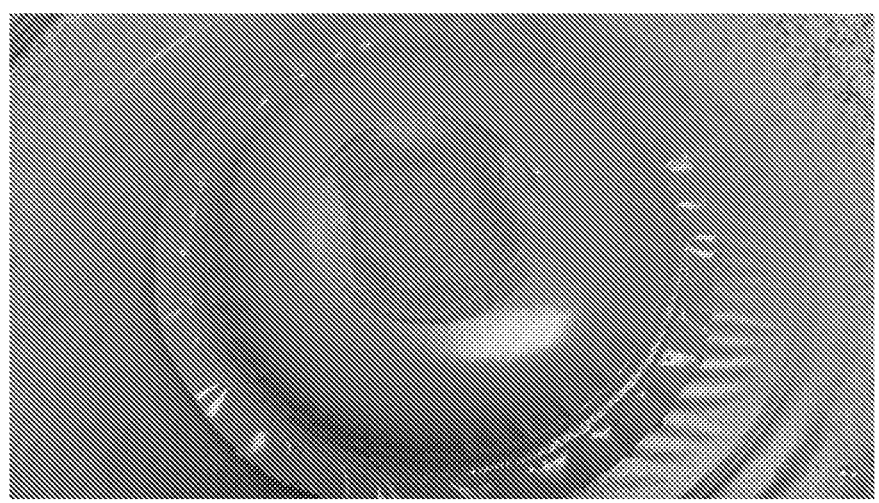

Sample B is shown in FIG. 3 before contact saline was added and in FIG. 4 after 2 minutes and where the foam was saturated with saline. It appears from FIG. 4 that the foam has swelled and expanded towards the stoma, thereby closing the gap between the stoma and the foam. A sealing against the stoma and the peristomal skin and adhesive edges has been provided and output from the stoma may have difficulties penetrating it.

The invention claimed is:
1. An ostomy element comprising:
 a backing layer;
 an adhesive disposed on a proximal surface of the backing layer, with the adhesive adapted to secure the ostomy element to skin around a stoma;
 a cover layer having an outer edge secured to a distal surface of the backing layer;

a swellable, absorbent foam disposed distal the adhesive and positioned between the backing layer and the cover layer; and a stoma-receiving through-going hole formed through the backing layer, the adhesive, the cover layer, and the swellable, absorbent foam;

wherein the swellable, absorbent foam is exposed on a surface of the stoma-receiving through-going hole and is configured, when wetted by an aqueous solution, to expand at least 50% V/V and move into the stoma-receiving through-going hole.

2. The ostomy element of claim 1, wherein the cover layer has an inner edge located at the stoma-receiving through-going hole, with the inner edge unsecured relative to the distal surface of the backing layer.

3. The ostomy element of claim 1, wherein the cover layer has an inner edge located at the stoma-receiving through-going hole, with the inner edge unsecured relative to the distal surface of the backing layer such that the cover layer forms a pocket with an open area exposed at the stoma-receiving through-going hole.

4. The ostomy element of claim 1, further comprising:
a paste located between the backing layer and the swellable, absorbent foam.

5. The ostomy element of claim 1, further comprising:
a paste deposited on the proximal surface of the backing layer and co-planar with the adhesive.

6. The ostomy element of claim 1, further comprising:
a moldable adhesive paste located between the backing layer and the swellable, absorbent foam.

7. The ostomy element of claim 1, further comprising:
a reservoir of liquid located between the swellable, absorbent foam and the cover layer.

8. The ostomy element of claim 1, further comprising:
a reservoir of liquid distal of the swellable, absorbent foam and located between the swellable, absorbent foam and the cover layer; and
a paste located proximal of the swellable, absorbent foam;
wherein pressure applied to the cover layer moves the liquid into the swellable, absorbent foam and forces the paste into the stoma-receiving through-going hole.

9. The ostomy element of claim 1, further comprising:
a base plate attachable to the ostomy element;
wherein the base plate is adapted to be secured to a user and the base plate is configured to couple with a removable ostomy bag.

10. The ostomy element of claim 1, wherein the swellable, absorbent foam is flush with the surface of the stoma-receiving through-going hole.

11. The ostomy element of claim 1, wherein the swellable, absorbent foam is adapted to expand when fully saturated with moisture between 100% v/v and 400% v/v and thus reduce an area of the stoma-receiving through-going hole.

12. The ostomy element of claim 1, wherein the swellable, absorbent foam has a proximal surface and a distal surface, and the proximal surface of the swellable, absorbent foam is configured to expand less than an expansion of the distal surface of the swellable, absorbent foam.

13. The ostomy element of claim 1, wherein the swellable, absorbent foam is free flowing characterized in that the swellable, absorbent foam is not attached to either of the backing layer or the cover layer.

14. The ostomy element of claim 1, wherein the cover layer is one of a non-woven, a fabric, a net, and a polymeric film.

15. The ostomy element of claim 1, wherein the cover layer is impermeable to liquid.

16. The ostomy element of claim 1, wherein the swellable, absorbent foam comprises polyurethane.

* * * * *